United States Patent [19]

Thomas

[11] 4,242,462
[45] Dec. 30, 1980

[54] ELECTRICALLY POWERED SELF-HEATING INOCULATING LOOP

[76] Inventor: Richard E. Thomas, 190 Windsor Ct., Athens, Ga. 30606

[21] Appl. No.: 20,999

[22] Filed: Mar. 16, 1979

[51] Int. Cl.³ .............................................. C12M 1/26
[52] U.S. Cl. .................................. 435/292; 435/293; 435/311
[58] Field of Search ................ 435/292, 293, 294, 311

[56] References Cited

U.S. PATENT DOCUMENTS

| | | | |
|---|---|---|---|
| 3,067,016 | 12/1962 | Rozycki | 23/259 |
| 3,436,171 | 4/1969 | Weichselbaum et al. | 435/311 X |
| 3,461,874 | 8/1969 | Martinez | 128/303.17 |
| 3,742,187 | 6/1973 | Folus | 435/292 X |
| 3,886,944 | 6/1975 | Jamshidi | 128/303.1 |
| 3,893,807 | 7/1975 | Cizinsky | 435/311 X |
| 3,935,075 | 1/1976 | Perry et al. | 435/293 |
| 3,938,526 | 2/1976 | Anderson | 128/303.1 |
| 4,074,110 | 2/1978 | Slaughter | 219/240 |
| 4,144,135 | 3/1979 | Sequeira | 435/293 |

Primary Examiner—R. B. Penland
Attorney, Agent, or Firm—Phillips, Hart & Mozley

[57] ABSTRACT

An electrically powered self-heating inoculating loop, including an inoculating loop capable of being heated by passing an electrical current through the loop, and a means for introducing and regulating the electrical current to said inoculating loop.

5 Claims, 4 Drawing Figures

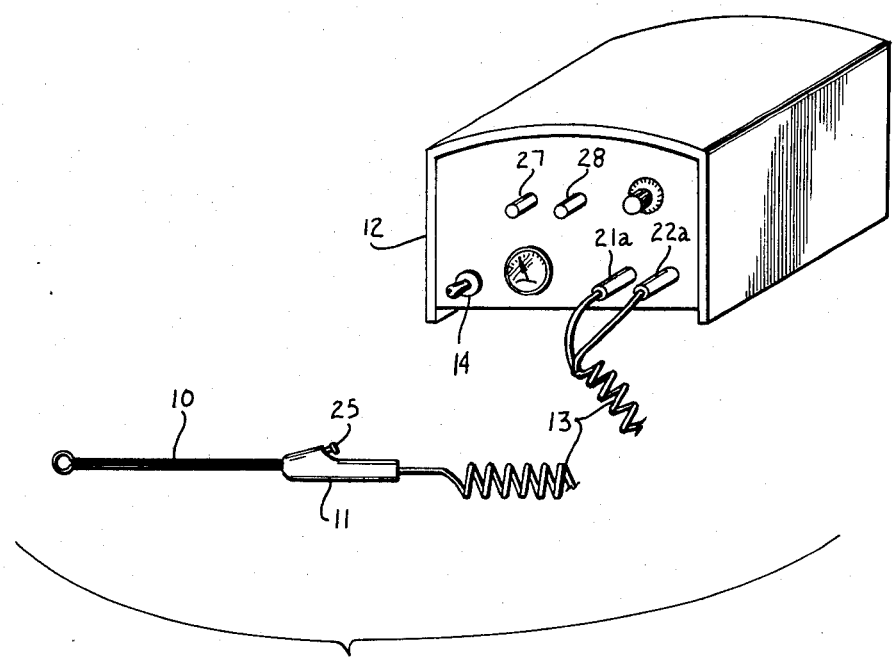
Fig_1
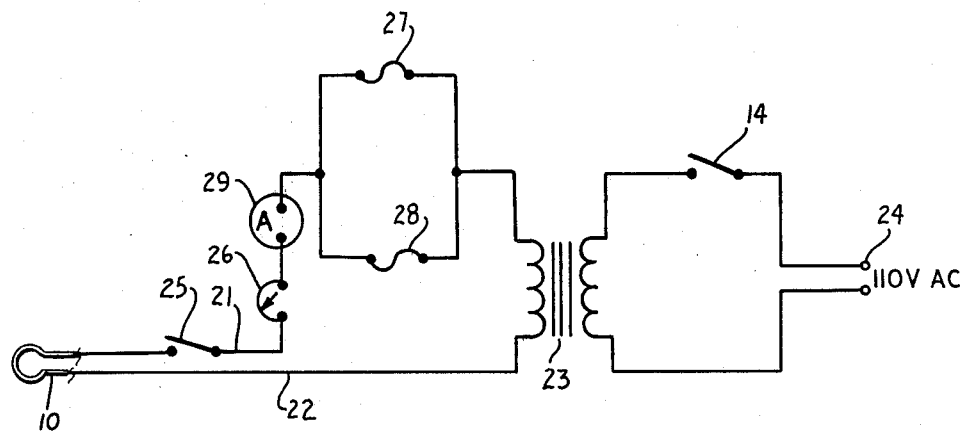
Fig_2

ELECTRICALLY POWERED SELF-HEATING INOCULATING LOOP

BACKGROUND OF THE INVENTION

The present invention relates to the art of providing a sterile medium for the transfer of bacteriological cultures and specimens from one container to another container without permitting contamination of the culture or specimen during the transfer procedure. More specifically, the present invention relates to providing a sterile inoculating loop by which the cultures and specimens may be transported during the transfer procedure.

Traditionally, inoculating loops have merely been long thin pieces of wire looped at one end which have been sterilized and used to transport cultures from one container to another container. The inoculating loops have been sterilized by the exposure of the wire to an external source of heat by which the wire is heated to the desired sterilization temperature.

The external source of heat most widely used for heating the inoculating loop is the laboratory Bunson Burner. Ordinarily, sterilization by use of a Bunson Burner requires heating the inoculating loop over the Bunson Burner for from ten to fifteen seconds before each transfer. Accordingly, laboratory procedures requiring numerous transfers of cultures and specimens are very laborious and time consuming using the traditional method of sterilizing the inoculating loop.

Further, the proper sterilization of the inoculating loop requires uniform heating over the length of the inoculating loop. Obviously, the localized source of heat provided by the Bunson Burner makes uniform heating difficult. Moreover, in laboratory procedures requiring numerous time consuming transfers, uniformity of heating is often sacrificed in practice to the desire to quickly heat the inoculating loop.

In addition to the traditional Bunson Burner, the prior art has included more sophisticated sources of external heating of inoculating loops. For example, a gas burner as shown in U.S. Pat. No. 3,893,807, issued on July 8, 1975 to Mr. Bedrich Cizinsky of Prague, Czechoslovakia, provides an apparatus for uniformly heating an inoculating loop, which apparatus intermittently provides a gas flame in the presence of the inoculating loop.

Another apparatus for external heating of an inoculating loop is shown in U.S. Pat. No. 3,436,171, issued on June 25, 1965 to Mr. T. E. Weicheselbaum and Mr. Phillip L. Varney. The Weichselbaum and Varney patent teaches the external heating of the inoculating loop by providing an infra-red heating device in which the inoculating loop may be heated to sterilization temperature.

SUMMARY OF THE INVENTION

The present invention is an electrically powered self-heating inoculating loop. The inoculating loop is capable of being uniformly heated to sterilization temperature by passing an electrical current through the inoculating loop.

It is an objective of the present invention to provide an inoculating loop which does not require an external heat source to heat the inoculating loop to the desired sterilization temperature.

It is a further objective of the present invention to provide an inoculating loop which may be quickly heated to sterilization temperature.

A still further objective of the present invention is to provide an inoculating loop which is uniformly heated to sterilization temperature.

An additional objective of the present invention is to provide an inoculating loop which provides a reliable indication that the inoculating loop has been uniformly heated to sterilization temperature.

The foregoing objectives and still further objectives of the present invention will become apparent from the consideration of the following Description of a Preferred Embodiment, and consideration of the attached Drawings in which the numbered parts described in the Description of a Preferred Embodiment are shown by like numbered parts in the accompanying Drawings.

DESCRIPTION OF THE DRAWINGS

FIG. 1 is a pictorial representation of one preferred embodiment of the present invention;

FIG. 2 is a schematic diagram of one preferred embodiment of the present invention;

DETAILED DESCRIPTION OF A PREFERRED EMBODIMENT

Figure 3:
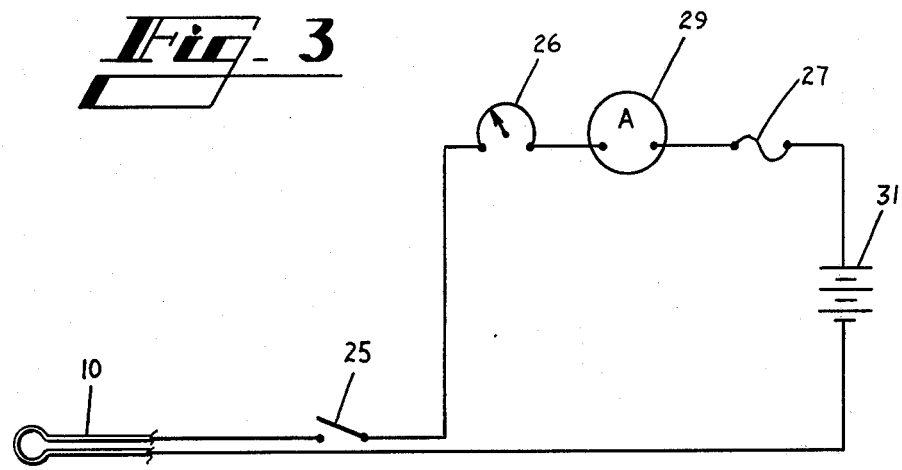
FIG. 3 is a schematic diagram of a second preferred embodiment of the present invention.

It will be understood that the following Description of a Preferred Embodiment is a description of only one exemplary embodiment of the present invention. The following Description of a Preferred Embodiment is not intended to be an exhaustive description of all of the alternative embodiments of the present invention, and it will be understood that the scope of the present invention and the alternative embodiments encompassed thereby is limited only by the appended claims.

The preferred embodiment of the present invention includes an inoculating loop 10 which is carried by handle 11. The handle 11 and the inoculating loop 10 are electrically connected to a control box 12 by a flexible electrical cord 13 containing at least two electrical wires 21 and 22. The electrical cord 13 may be removable and may be electrically connected to the control box 12 by a pair of removable electrical connectors 21a and 22a. As will be described more fully below, the control box 12 contains the control circuitry for the preferred embodiment and also the circuitry for introducing electrical power to the inoculating loop 10.

Figure 4:
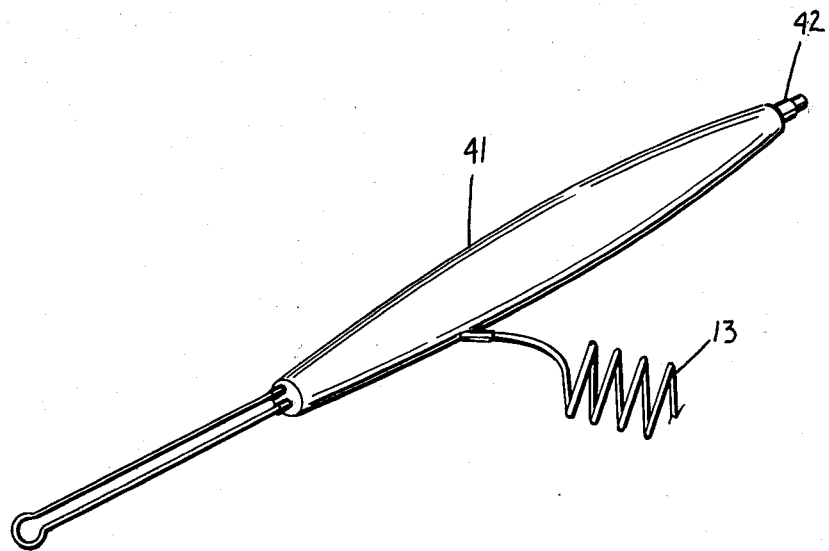
FIG. 4 is a pictorial representation of an alternative embodiment of the handle for the inoculating loop.

As shown in FIG. 4, the design of the handle for the inoculating loop may be varied to facilitate different methods of handling the inoculating loop 10. Thus, as shown by the handle 41, the handle may be designed such that the inoculating loop may be held between the thumb and the forefingers of the operator's hand. A switch 42 may be provided at the remote end of the handle 41 for initiating the heating of the inoculating loop 10. Alternatively, as shown in FIG. 1, the handle 11 may be designed such that the handle 11 is grasped by the fingers of the operator's hand, and the switch 25 for initiating the heating process may be operated by the thumb of the operator's hand. Of course, it will be understood that the handle of the inoculating loop may be designed in other ways to facilitate the varied desired methods of handling the inoculating loop.

The inoculating loop 10 may be made from any material capable of being heated to sterilization temperature by passing an electrical current through loop 10.

Generally, the inoculating loop 10 will be made from an elongated piece of metallic wire having a thin cross-sectional diameter. The metallic wire is heated by passing an electrical current through the inoculating loop 10, and heating the inoculating loop 10 according to the principles of joule or resistance heating.

The sensitivity of the resistivity of the specific material used for the loop to changes in temperature of the material, as well as the cross-sectional diameter of the material, will determine the usefulness of the material as an inoculating loop according to the present invention. The rate of heating of the inoculating loop 10 as an electrical current is passed through the inoculating loop 10 will vary according to the foregoing material and physical characteristics of the metallic wire used. If the initial resistivity of the material is high and if the resistivity of the material is too insensitive to changes in temperature, the material may not be capable of being heated to sterilization temperature without an undue use of the electrical power. On the other hand, if the initial resistivity of the material is too low and the resistivity of the material is too sensitive to changes in temperature, the utility and accuracy of the present invention will be impaired.

The cross-sectional diameter of the material used for the inoculating loop 10 will affect both the rate of heating and the energy required to heat the inoculating loop 10 to sterilization temperature. Depending upon the electrical power available to heat the inoculating loop 10, a narrower cross-sectional diameter of the material used for the inoculating loop 10 will result in more rapid heating of the inoculating loop 10. Similarily, the more rapid the heating of the inoculating loop 10, and the narrower the cross-sectional diameter of the material used for the inoculating loop 10, the less electrical energy will be required to heat the inoculating loop 10 to sterlization temperature.

It has been found that the standard commercially available materials for use in inoculating loops are suitable for use in the present invention. Thus, commercially available high resistance non-corrosive platinum-chromium alloy inoculating loop wires having a gauge within the range of 0.015 inches to 0.036 inches has been found suitable for use in the inoculating loop 10. Further, other commercially available materials suitable for use in fabricating the inoculating loop 10 of the present invention are nichrome wire and tungsten alloy wire.

The source of electrical power for the preferred embodiment described herein and shown in FIGS. 1 and 2 is a standard 110 volt A.C. external power source 24 which may be switched on and off by power switch 14. In the preferred embodiment described herein, and shown in FIGS. 1 and 2, the 110 A.C. current is introduced to a suitable transformer 23 which converts the electrical energy from the external power source 24 to D.C. current which will ultimately be introduced into inoculating loop 10. The electrical power for the present invention may also be provided by a self-contained source of electrical energy such as standard batteries or rechargeable electrical batteries such as nickel-cadmium batteries 31 as shown in FIG. 3. The circumstances under which the self-heating inoculating loop is to be used will determine whether a self-contained source of electrical energy is needed or whether an external source of electrical energy is available and is sufficient to provide electrical power to the electrically powered self-heating inoculating loop.

The electrical current from the transformer 23 is introduced to a control circuit including: a switch 25 in series with the inoculating loop 10 which is used for initiating the flow of current through the inoculating loop 10; a rheostat 26 in series with the inoculating loop 10 which is used for varying the resistance in the circuit containing the inoculating loop 10; and at least a first circuit breaker 27 in series with the inoculating loop 10, but preferably also including a second circuit breaker 28 in series with the inoculating loop 10 and in parallel with the first circuit breaker 27.

The purpose of the switch 25 is to provide easily accessible means for initiating and controlling the flow of current to the inoculating loop 10. As shown in both FIG. 1 and FIG. 4, the switches 25 and 42 may be button switches which are only closed when pressure is applied to the button. In this manner, the safety of the present invention is enhanced.

The purpose of the parallel circuit breakers 27 and 28 is to provide control over the maximum temperature to which the inoculating loop 10 is heated, and also to provide a reliable indicator to show that the inoculating loop 10 has reached sterilization temperature. If a lesser sterilization temperature is desired, then only circuit breaker 27, having a value greater than circuit breaker 28, is set. Once the current through the inoculating loop 10 increases to the value of the circuit breaker 27 in response to the reduction in resistance in the inoculating loop 10 when heated to the desired sterilization temperature, then the circuit breaker 27 will open, preventing any further current from flowing into the inoculating loop 10 and thereby stopping the further heating of the inoculating loop 10.

If the greater sterilization temperature is desired, then only the circuit breaker 28, having a value lower than circuit breaker 27, should be set. The circuit breaker 28, having a lower value than circuit breaker 27, will permit the inoculating loop to heat to a greater temperature, as indicated by a greater current flow through the inoculating loop 10 before opening the circuit breaker 28 and stopping the flow of electrical current to the inoculating loop 10.

Greater control over the heating of the inoculating loop 10 may also be provided by the rheostat 26. By adjusting the rheostat 26 to increase the resistance in series with the inoculating loop 10, the resistance of the inoculating loop 10 will be required to diminish by a greater magnitude before the circuit breakers 27 or 28 will open and stop the flow of current and the heating of the inoculating loop 10. Indeed, the presence of rheostate 26 in the circuit may obviate the need for the second circuit breaker 28 having the lower value, since the higher temperature may be achieved merely by setting the rheostat 26 to a higher value.

Finally, the addition of an ammeter 29 in series with the inoculating loop 10 will permit the heating of the inoculating loop 10 to be monitored. Of course, if the ammeter 29 is used, the indicator function of the circuit breaker 27 and 28 is no longer necessary and the switching function of the circuit breakers 27 and 28 may be manually controlled by the switch 25. Accordingly, the circuit breakers 27 and 28 may be omitted or may be adjusted to a sufficiently low value that the circuit breakers 27 or 28 provide primarily a safety function to prevent the inoculating loop 10 from overheating.

The preferred embodiment described above may be operated in the following manner. Depending upon the material used for the inoculating loop 10 and the desired temperature to which the inoculating loop 10 is to be heated, the circuit breaker 27 or the circuit breaker 28 is set. For further adjustments in the temperature to which the inoculating loop 10 is to be heated, the value of the rheostat 26 may be either increased or decreased in order to either increase or decrease the temperature to which the inoculating loop 10 will be heated before the set circuit breaker 27 or 28 will open and stop the heating of the inoculating loop 10.

The switch 25 is then closed, allowing the flow of current through the inoculating loop 10 to begin. The inoculating loop 10 is then heated until the set circuit breaker 27 or 28 opens, or until the ammeter 29 indicates that the inoculating loop 10 has been heated to sterilization temperature. It has been found that an inoculating loop 10 made from a standard gauge platinum-chromium inoculating loop wire will heat to sterilization temperature in approximately two seconds when the circuit breaker 27 is set and has a value of 3.5 amps and no resistance has been added by rheostat 26. It is believed that the sterilization temperature achieved in this manner is at least 1,200 degrees centigrade.

Once the inoculating loop 10 has been heated to sterilization temperature, it may be used to transfer cultures or specimens in the conventional manner. In addition, the heated inoculating loop 10 may also be used to heat and sterilize other laboratory objects, such as test tubes, and also to perform other standard laboratory functions such as the fixation of gram stains.

It will be understood by those skilled in the art that the foregoing Description of a Preferred Embodiment has not been exhaustive of the various alternative embodiments of the present invention, and has been merely illustrative and exemplary of the preferred embodiments of the present invention. It will be understood that additional embodiments clearly fall within the spirit and scope of the present invention, and that the present invention is limited solely by reference to the appended claims.

What I claim is:

1. An electrically powered inoculating loop which is heated to sterilization temperature by passing an electrical current, introduced from a source of electrical power, through the inoculating loop, comprising:
   (a) an inoculating loop made of material suitable for heating to sterilization temperature by passing an electrical current through said loop;
   (b) a means for introducing an electrical current from said source of electrical power to said inoculating loop; and
   (c) a first temperature control circuit breaker means responsive to the temperature of the inoculating loop for discontinuing the electrical current from said source of electrical power to said inoculating loop when the temperature of said inoculating loop reaches sterilization temperature.

2. An inoculating loop as set forth in claim 1, further including a second temperature control circuit breaker means responsive to the temperature of the inoculating loop for discontinuing the electrical current from said source of electrical power to said inoculating loop when the temperature of said inoculating loop reaches a second sterilization temperature.

3. An inoculating loop as set forth in claim 2 wherein said second temperature control circuit breaker means is of different amperage value from said first circuit breaker, said second circuit breaker being connected in parallel with said first circuit breaker between said source of electrical power and said inoculating loop.

4. An inoculating loop as set forth in claim 1, wherein said means for introducing an electrical current from said source of electrical power to said inoculating loop includes an electrical circuit and a means for varying the resistance of said electrical circuit.

5. An inoculating loop as set forth in claim 4, wherein said means for varying the resistance of said electrical circuit includes a rheostat.

* * * * *